(12) United States Patent
Kantor et al.

(10) Patent No.: US 8,515,007 B2
(45) Date of Patent: Aug. 20, 2013

(54) MOTION SYSTEM FOR PANORAMIC DENTAL RADIATION IMAGING SYSTEM

(75) Inventors: Arkady Kantor, Buffalo Grove, IL (US); Donald Walker, Mundelein, IL (US); Lyubomir L. Cekov, Rolling Meadows, IL (US); Alan P. Krema, Naperville, IL (US)

(73) Assignee: Midmark Corporation, Versailles, OH (US)

( * ) Notice: Subject to any disclaimer, the term of this patent is extended or adjusted under 35 U.S.C. 154(b) by 783 days.

(21) Appl. No.: 12/638,624

(22) Filed: Dec. 15, 2009

(65) Prior Publication Data

US 2011/0142199 A1    Jun. 16, 2011

(51) Int. Cl.
    *A61B 6/14*    (2006.01)

(52) U.S. Cl.
    USPC ............................................................. 378/39

(58) Field of Classification Search
    USPC ...................................... 378/38, 39, 193–198
    See application file for complete search history.

(56) References Cited

U.S. PATENT DOCUMENTS

| | | | |
|---|---|---|---|
| 4,741,007 A | 4/1988 | Virta et al. | |
| 5,425,065 A | 6/1995 | Jarvenin | |
| 5,511,106 A | 4/1996 | Doebert et al. | |
| 5,732,119 A | 3/1998 | Kopsala | |
| 6,466,641 B1 | 10/2002 | Virta et al. | |
| 6,510,196 B2 | 1/2003 | Laner | |
| 6,553,095 B2 | 4/2003 | Rinaldi et al. | |
| 6,731,717 B2 | 5/2004 | Kopsala | |
| 6,744,847 B2 | 6/2004 | Martti | |
| 6,829,326 B2 | 12/2004 | Woods et al. | |
| 6,891,921 B2 | 5/2005 | Kopsala | |
| 7,409,036 B2 * | 8/2008 | De Godzinsky et al. | 378/39 |
| 2007/0269001 A1 * | 11/2007 | Maschke | 378/38 |

* cited by examiner

*Primary Examiner* — Irakli Kiknadze
(74) *Attorney, Agent, or Firm* — Wood, Herron & Evans, LLP

(57) ABSTRACT

A motion system for use in a panoramic dental radiation imaging system, including apparatus for rotating an overhead arm with respect to a support column, apparatus for rotating a C-arm with respect to the overhead arm, and apparatus for moving the C-arm axially with respect to the overhead arm. The overhead arm is rotatably mounted to the support column at a rotation point. The apparatus for rotating the overhead arm is a linear actuator, one end of which is connected to the support column at a first point spaced apart from the rotation point, while the other end is connected to the overhead arm at a second point spaced apart from the rotation point and from the first point. The C-arm rotating apparatus includes a C-arm rotation motor driving a wheel, which is engaged with the C-arm in such a way that the rotation of the wheel causes rotation of the C-arm.

8 Claims, 15 Drawing Sheets

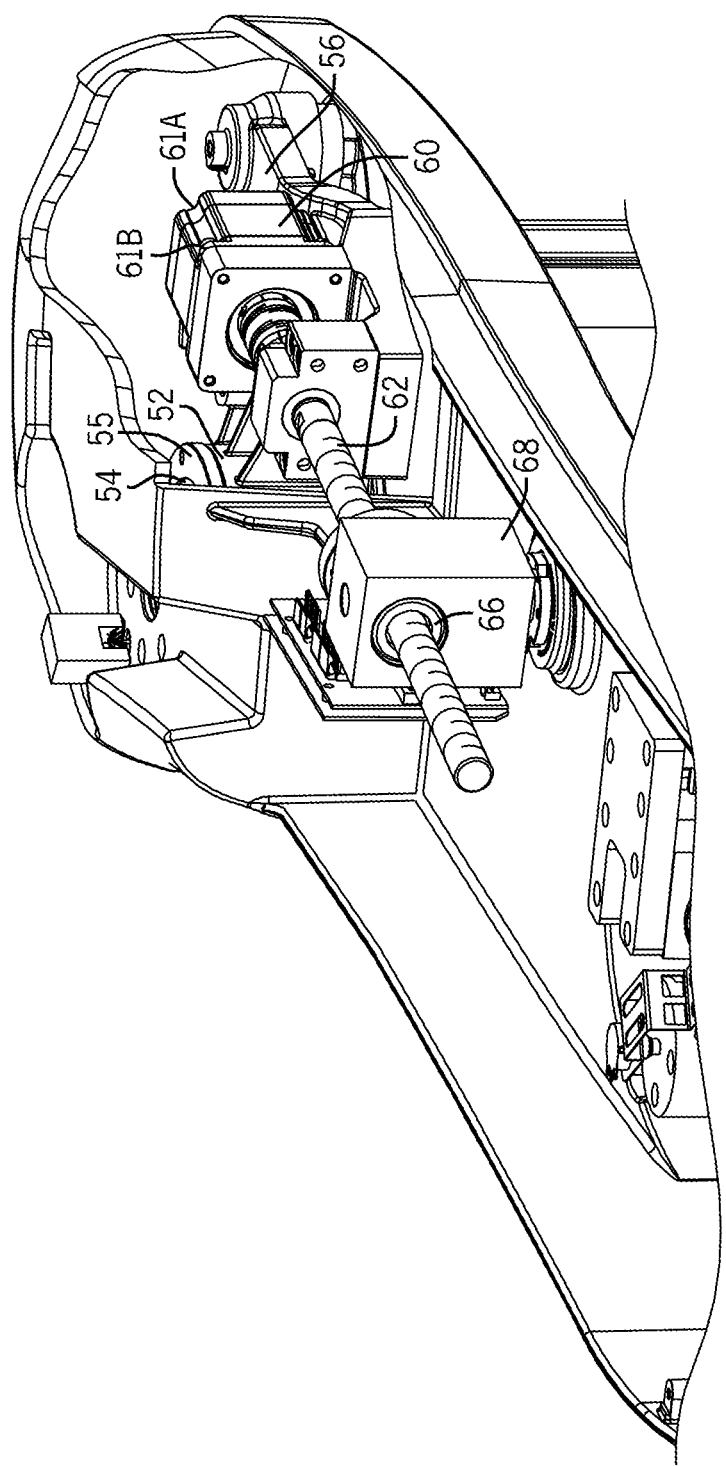

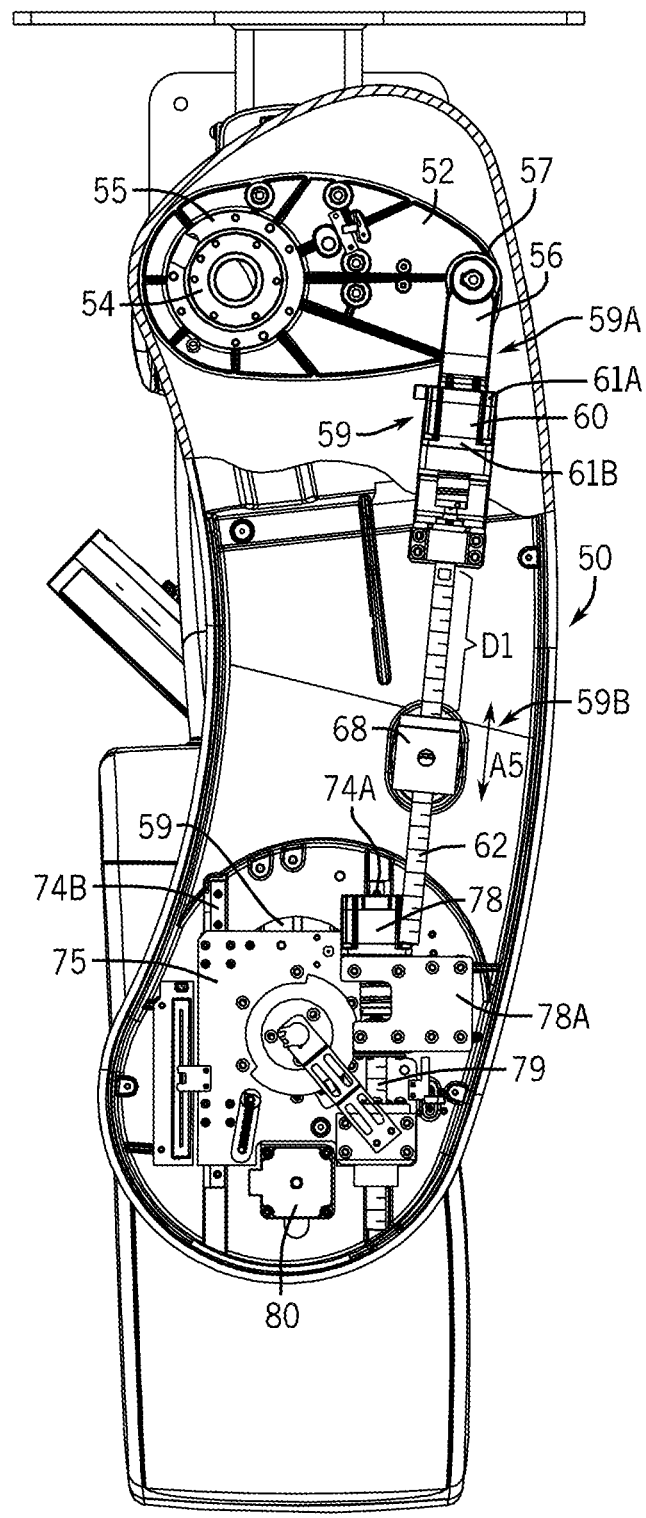

MOTION SYSTEM FOR PANORAMIC DENTAL RADIATION IMAGING SYSTEM

BACKGROUND OF THE INVENTION

This invention relates to dental radiation imaging systems, and in particular to systems for moving a radiation source and detector so as to produce panoramic images.

Panoramic dental radiation is used to obtain images of a patient's teeth in an orthogonal manner. Since the dental arch is not a circular shape, or often even any type of regular shape, the rotation of the arm to which the radiation source and detector are attached must be adjusted in the course of the imaging in order to achieve the proper orthogonal imaging. Conventional panoramic radiation apparatuses are characterized in that the radiation source is arranged to orbit about the patient's skull, whereby the dental arch can be imaged by means of a radiation detector orbiting on the opposite side of the skull. The function of the rotating mechanism of a panoramic radiation apparatus is to direct the radiation beam through the patient's jaw at a desired angle and to keep the radiation detector at a particular distance from the object being imaged.

The radiation source of the panoramic radiation system and the rotating mechanism of its radiation detector must be capable of forming an image of the dental arch. During the rotational movement, the center of rotation is moved in order to ensure orthgonality of the radiation beam on the dental arch, constant magnification and focus, and continuity of motion. The rotating mechanism must be able to accomplish the desired orbital movement of the center of rotation in a horizontal plane (or other plane as desired) and provide vertical support to the entire apparatus so that the desired orbit can be implemented with accuracy.

Such orbital movement can be achieved by virtue of different conventional rotating mechanisms. A combination of linear movement with rotational movement, such as that disclosed in U.S. Pat. No. 4,741,007, may be used. However, the movement has been found problematic due to the precise accuracy required of the orbital movement, that is, it is more difficult to obtain the same accuracy for the mechanism of the orbital movement when a linear movement is involved than when a rotational movement is employed alone.

In U.S. Pat. No. 6,466,641, rotational movement is accomplished using orbital movement of several body parts of the system operating independently from each other. This system is very complicated and expensive.

The present invention relates to improvements to the apparatus described above and to solutions to some of the problems raised or not solved thereby.

SUMMARY OF THE INVENTION

Accordingly, the need exists, and the present invention provides, for a panoramic dental radiation imaging system that achieves the proper orthogonal imaging of a patient's dental arch with accuracy and continuity of movement, a design that can be manufactured at a reasonable cost using fewer movable bodies to produce the orbital movement, and which is simpler, less costly, and without the unnecessary motion of the apparatus in the prior art.

The present invention provides panoramic dental radiation imaging, and in particular provides a motion system for a panoramic dental radiation imaging system to achieve desired positioning of the radiation source and receiver to image a patient's dental arch, in which movement of various components of the system provides for movement of the radiation source and receiver in the necessary orbital pattern to achieve the desired image.

Specifically, the invention provides a motion system for use in a panoramic dental radiation imaging system, including a radiation source, a radiation sensor capable of receiving and detecting radiations, a C-arm to which the radiation source and radiation sensor are mounted, an overhead arm to which the C-arm is rotatably mounted; and a support column to which the overhead arm is rotatably mounted. According to the invention, the motion system includes apparatus for rotating the overhead arm with respect to the support column, apparatus for rotating the C-arm with respect to the overhead arm, and apparatus for moving the C-arm axially with respect to the overhead arm. The overhead arm is rotatably mounted to the support column at a rotation point. The apparatus for rotating the overhead arm is a linear actuator, one end of which is connected to the support column at a first point spaced apart from the rotation point, while the other end is connected to the overhead arm at a second point spaced apart from the rotation point and from the first point. The apparatus for rotating the C-arm with respect to the overhead arm includes a C-arm rotation motor mounted to the overhead arm. The rotation motor drives a wheel, which is engaged with the C-arm in such a way that the rotation of the wheel causes rotation of the C-arm. A linear actuator is provided for moving the C-arm axially with respect to the overhead arm.

Other objects and advantages of the invention will become apparent hereinafter.

BRIEF DESCRIPTION OF THE DRAWINGS

FIG. 5A is a detail perspective view of a proximal portion of the overhead arm of a panoramic dental radiation imaging system in accordance with an embodiment of the present invention, with portions cut away to reveal operational details inside;

FIG. 5B is a top view of a panoramic dental radiation imaging system in accordance with the embodiment shown in FIG. 5A, with portions cut away to reveal operational details inside;

DETAILED DESCRIPTION

Figure 1:
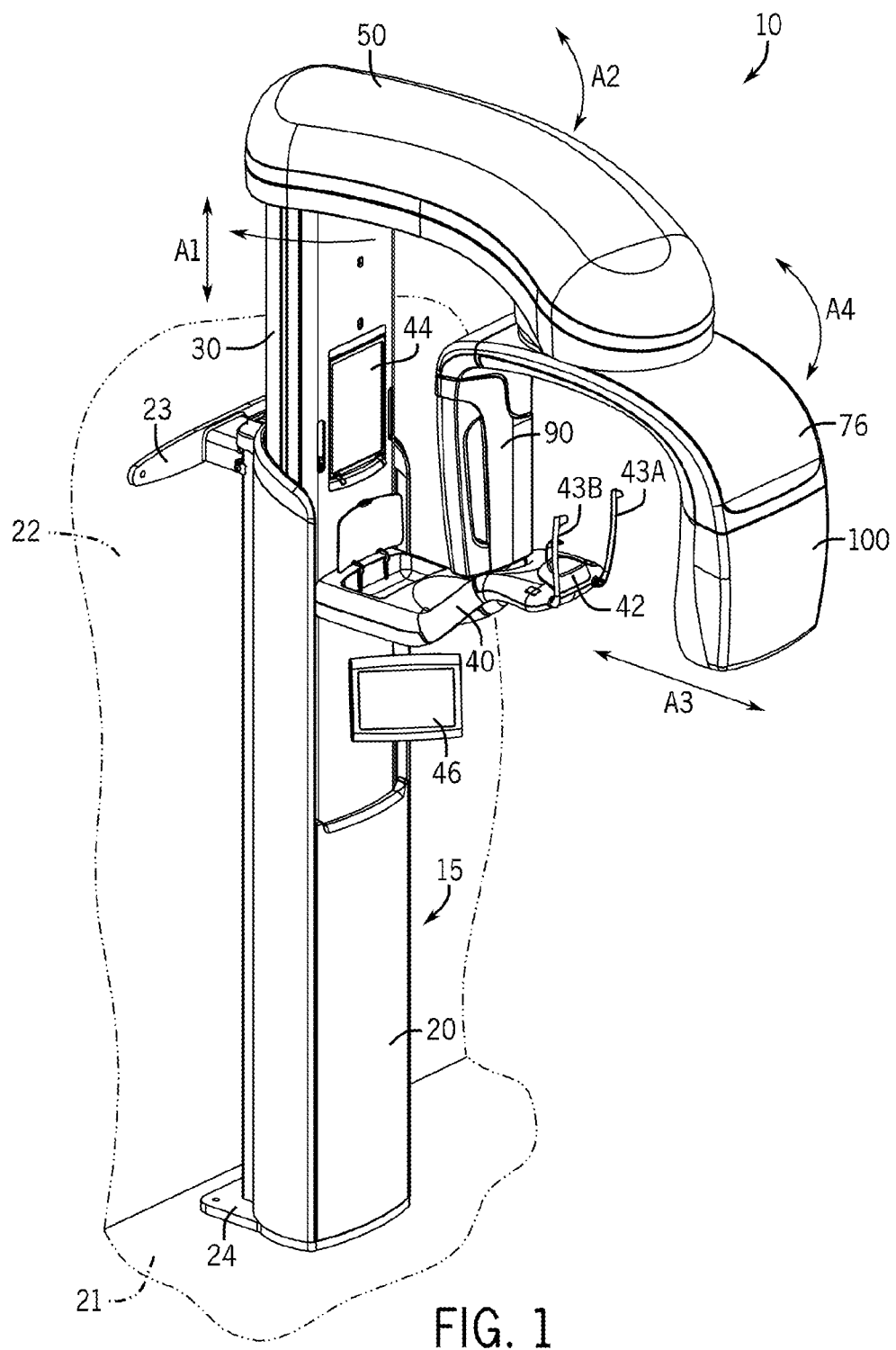
FIG. 1 is a side perspective view of a panoramic dental radiation imaging system in accordance with one embodiment of the present invention.

This application is being filed at the same time as a patent application on a patient positioning system for a panoramic dental radiation imaging system, and a patent application on a removable radiation sensor for a dental imaging system, and a design patent application on a dental imaging system, all filed on the same day as this application and assigned to the same assignee. The disclosure of each of those other patent applications is incorporated herein by reference.

One embodiment of a panoramic dental radiation imaging system 10 and motion system therefor is shown in the figures. While the invention may be susceptible to embodiment in different forms, there is shown in the drawings, and herein will be described in detail, certain illustrative embodiments with the understanding that the present disclosure is to be considered an exemplification of the principles of the invention, and is not intended to limit the invention to those as illustrated and described herein. Additionally, features illustrated and described with respect to one embodiment could be used in connection with other embodiments.

FIG. 1 shows a panoramic dental radiation imaging system 10. The imaging system 10 is used for examination of a dental patient's teeth, and generally includes a support column 15, which can also be referred to as an upright support, formed of an outer column 20, and an inner column 30, telescopically mounted within the outer column. An overhead arm 50 is mounted at its proximal end at the top of the upright support 15, and a C-arm 70 is mounted at the distal end of the overhead arm. C-arm 70 includes a radiation source 90 at the end of one of its legs, and a radiation receiver 100 at the end of the other of its legs. As will be explained in more detail, the radiation receiver 100 may be removable from the C-arm 70. Also, a patient positioning arm 40 may be mounted to the upright support 15 so as to assist in positioning the patient for accurately taking the radiation imaging.

Figure 2:
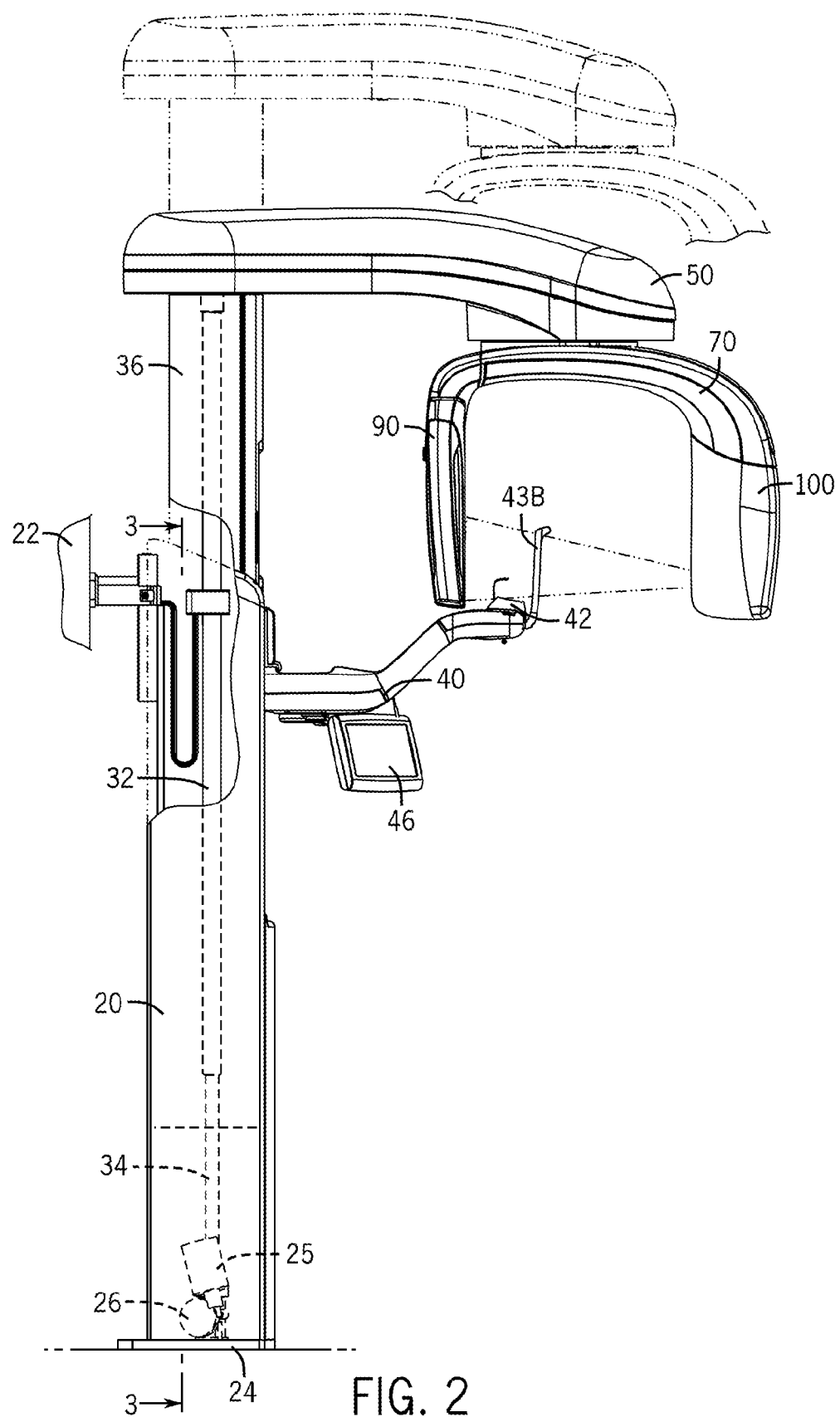
FIG. 2 is a side view of a panoramic dental radiation imaging system shown in FIG. 1, showing one position of a movable portion of the system in phantom.
Figure 3:
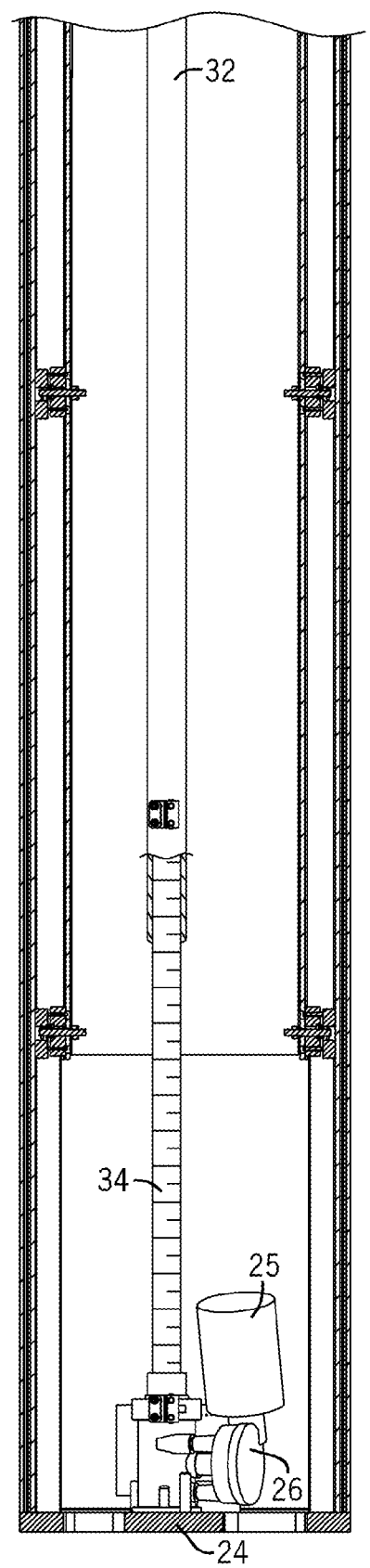
FIG. 3 is cross sectional view taken along line 3-3 of FIG. 2.
Figure 4:
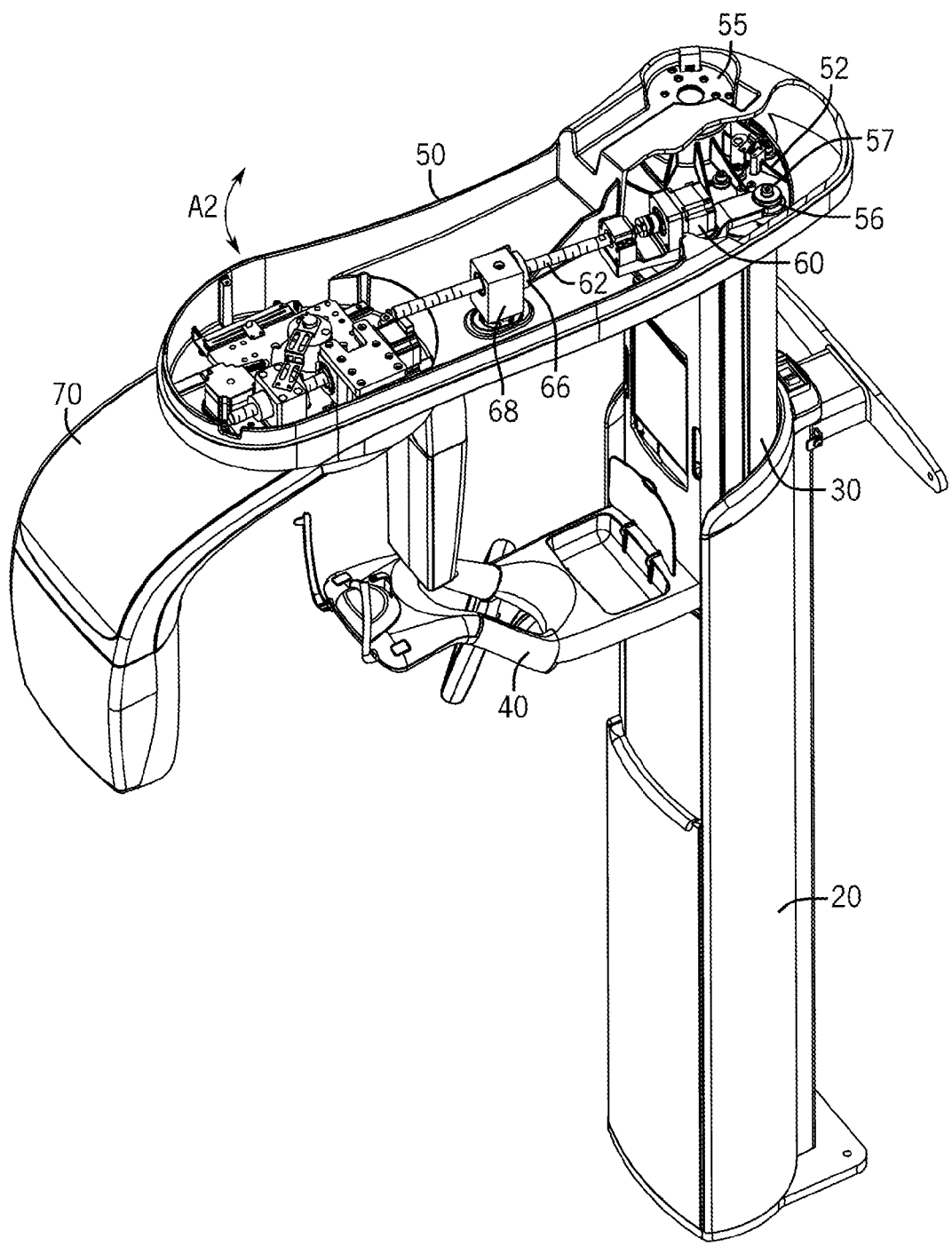
FIG. 4 is a top perspective view of a panoramic dental radiation imaging system in accordance with the embodiment shown in FIG. 1, with a portion of the top cover cut away to reveal operational details inside.
Figure 5C:
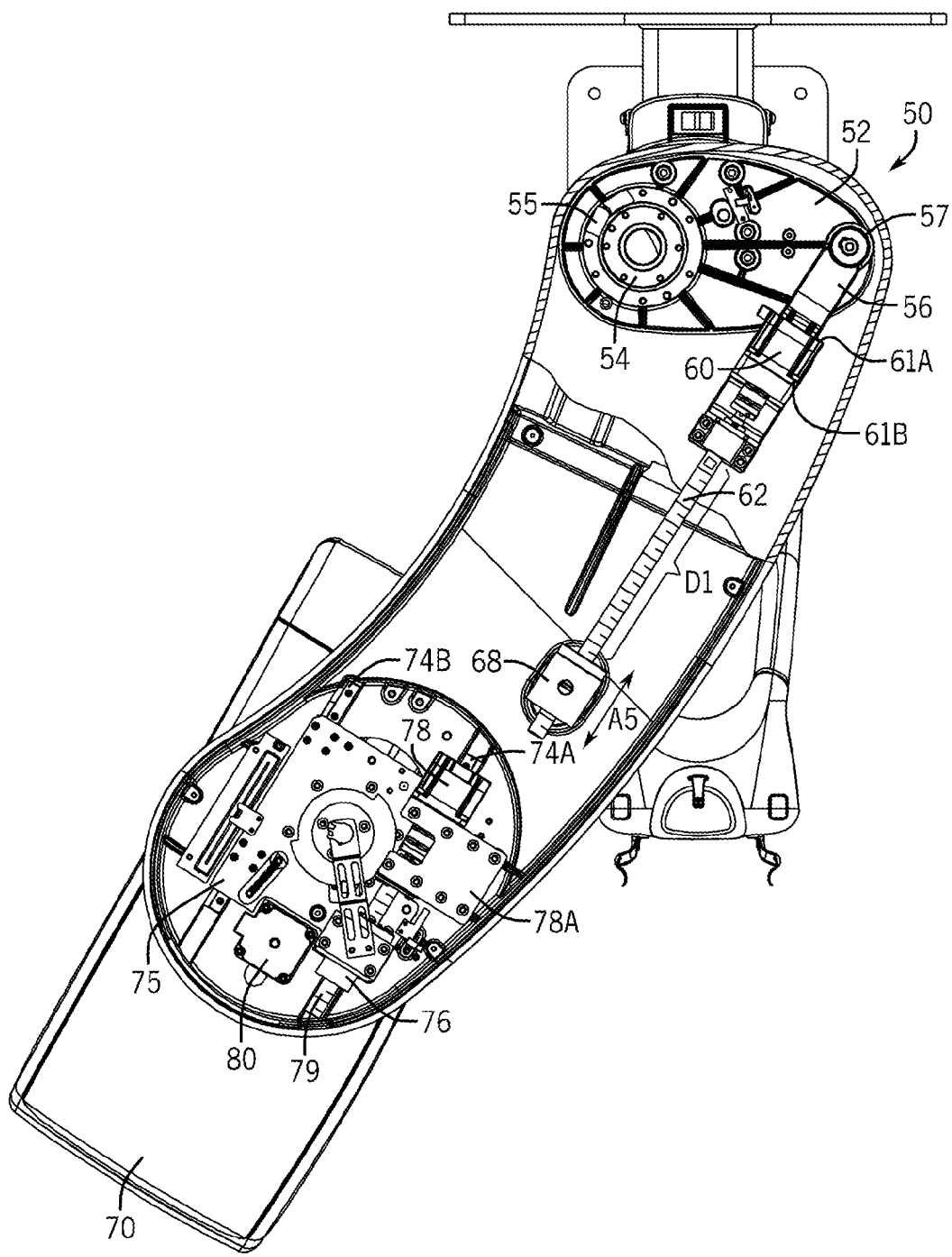
FIG. 5C is a top view of a panoramic dental radiation imaging system shown in FIG. 5B, with overhead arm rotated to a different position.
Figure 5D:
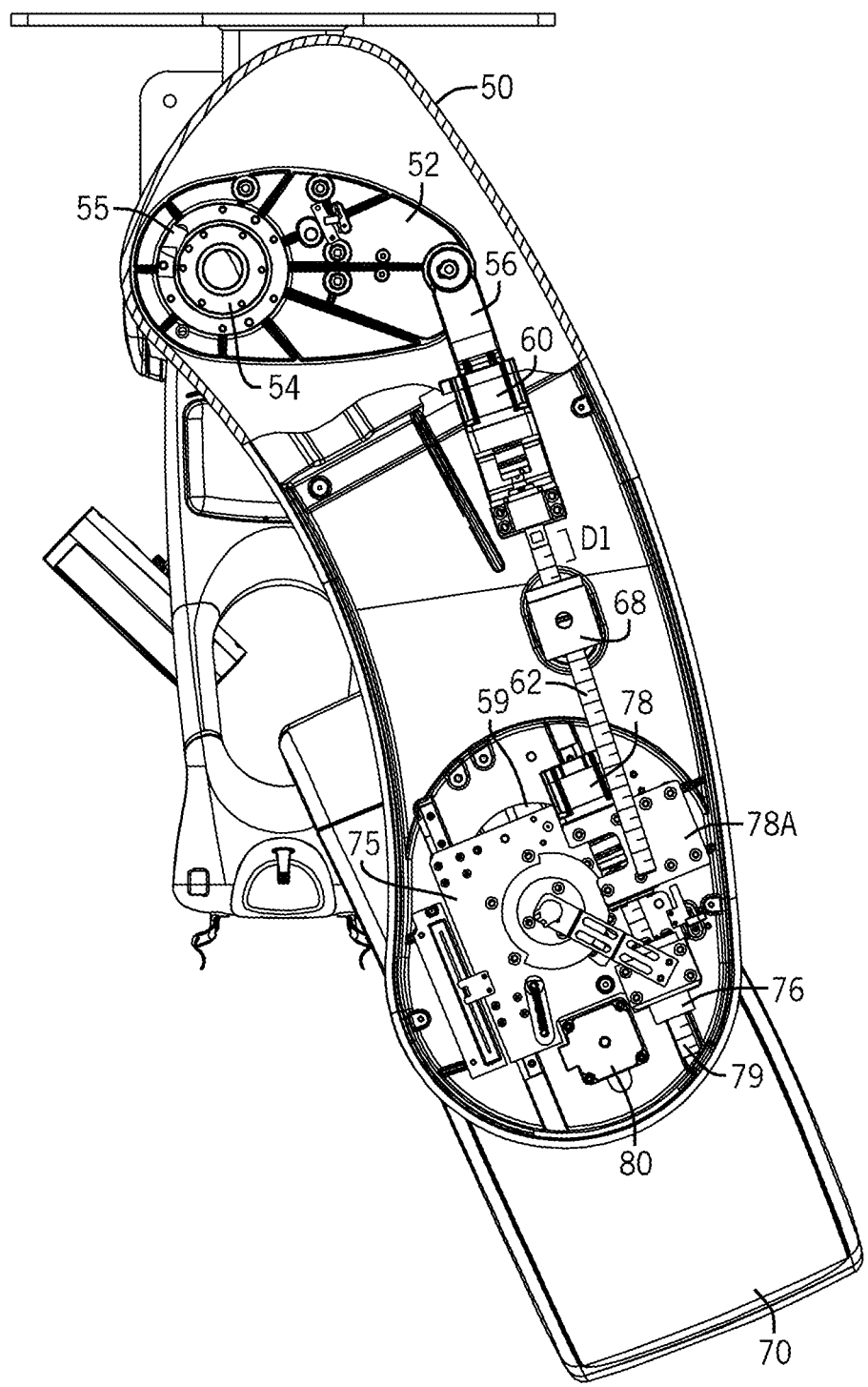
FIG. 5D is a top view of the panoramic dental radiation imaging system shown in FIG. 5B, with overhead arm rotated in a different direction than that shown in FIG. 5C.
Figure 6:
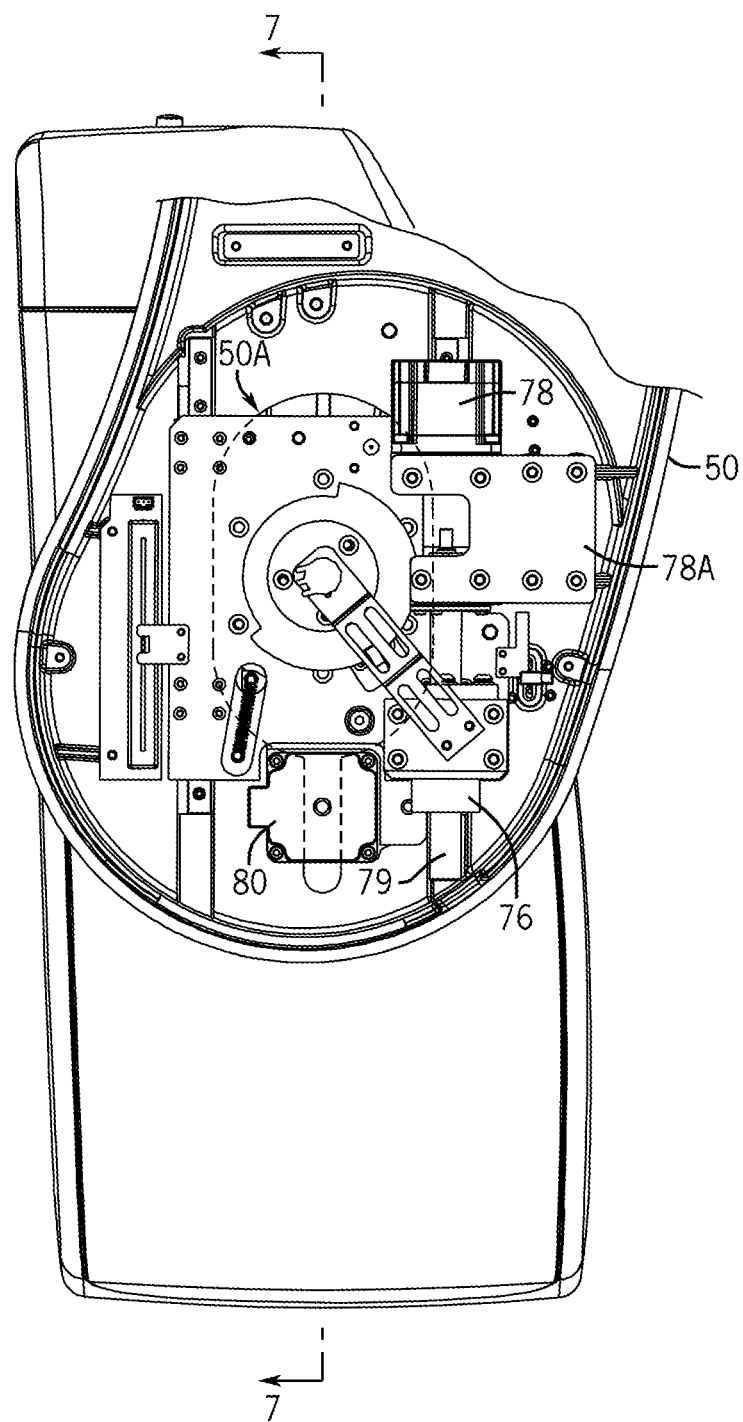
FIG. 6 is a top detail view of a distal portion of a panoramic dental radiation imaging system in accordance with one embodiment of the present invention, with a portion cut away to reveal operational details inside.
Figure 7:
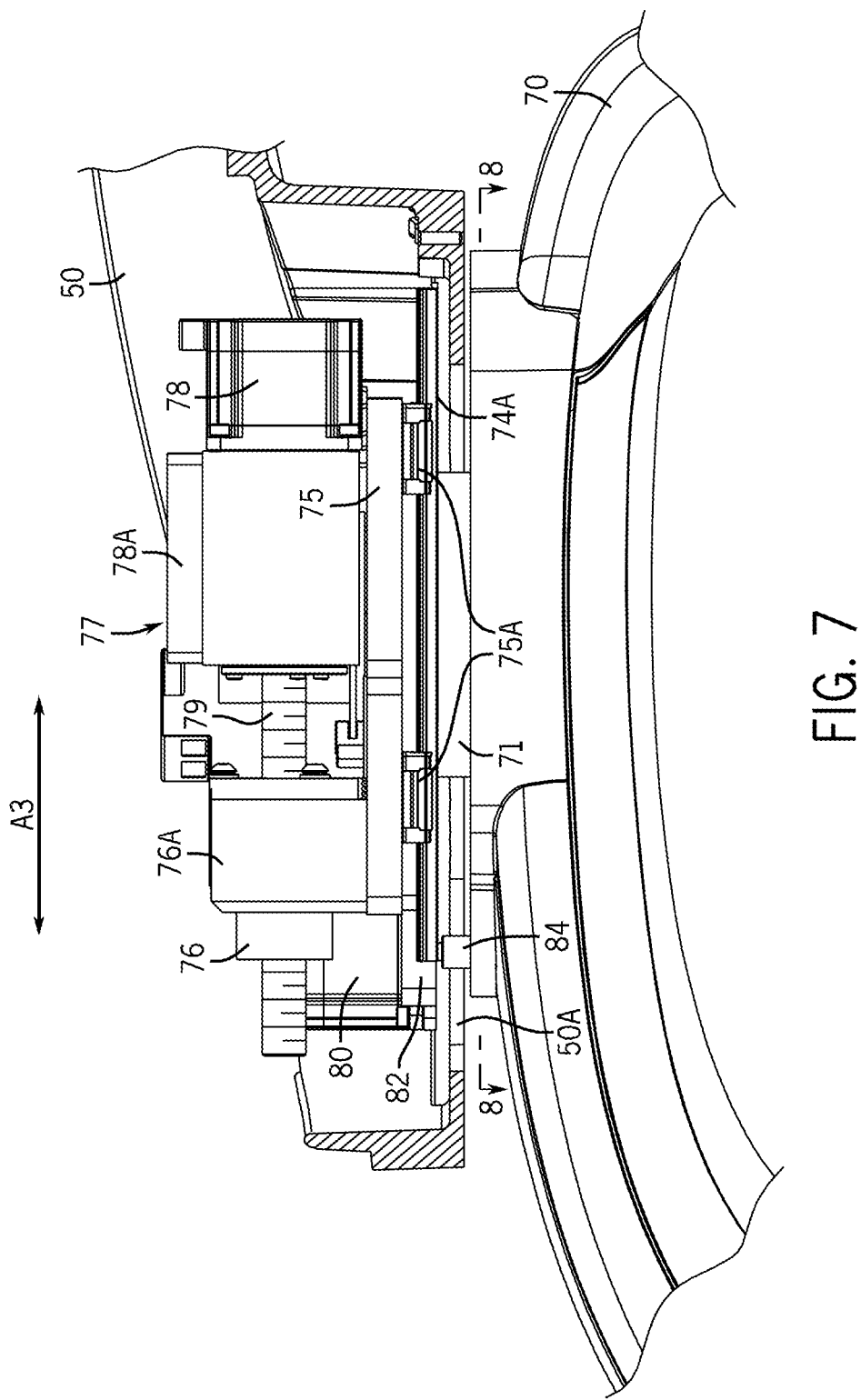
FIG. 7 is a cross sectional view of the embodiment shown in FIG. 6, taken along line 7-7 of FIG. 6.
Figure 7A:
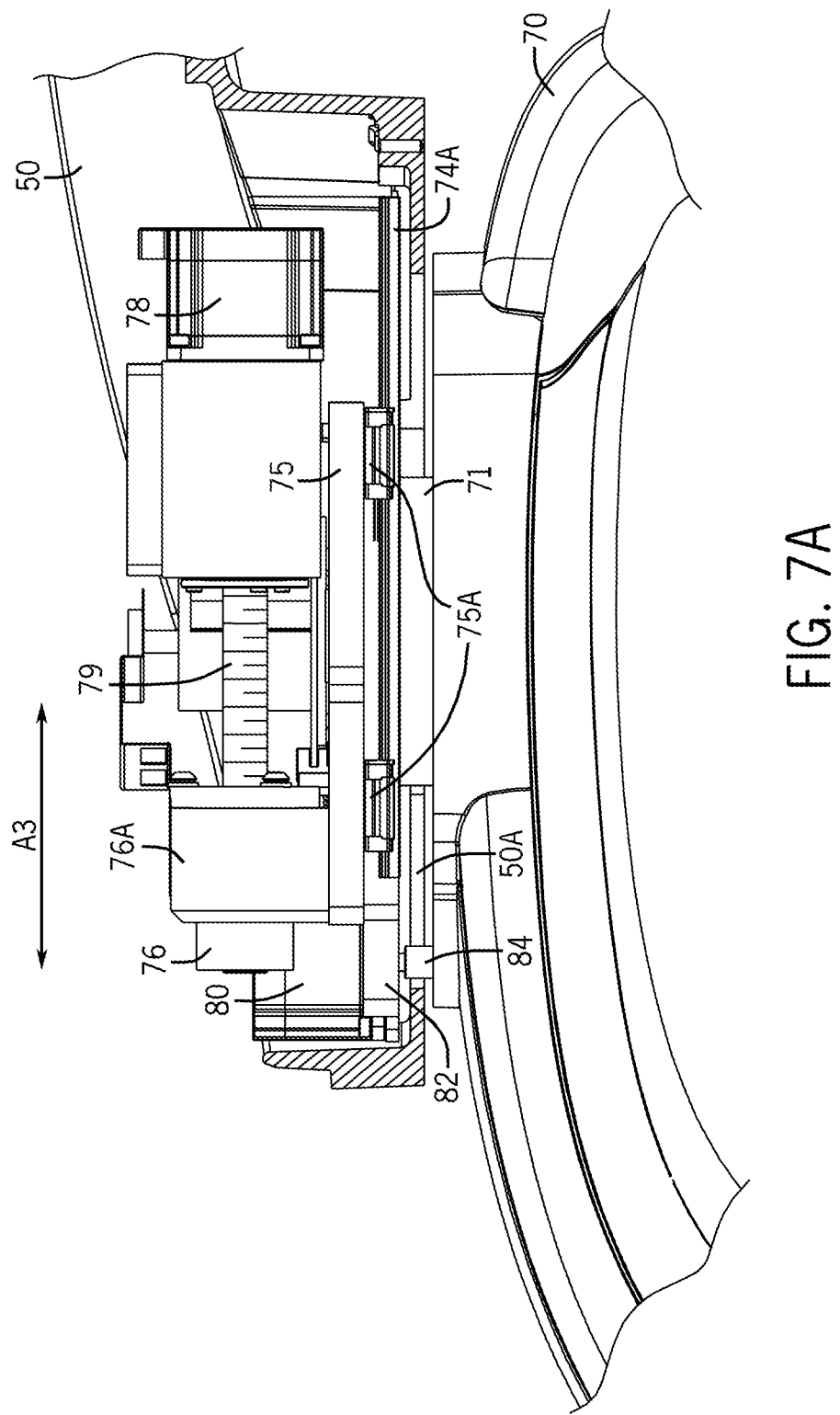
FIG. 7A is a cross sectional view of the panoramic dental radiation imaging system similar to FIG. 7, but in an alternate position to that shown in FIG. 7.
Figure 7B:
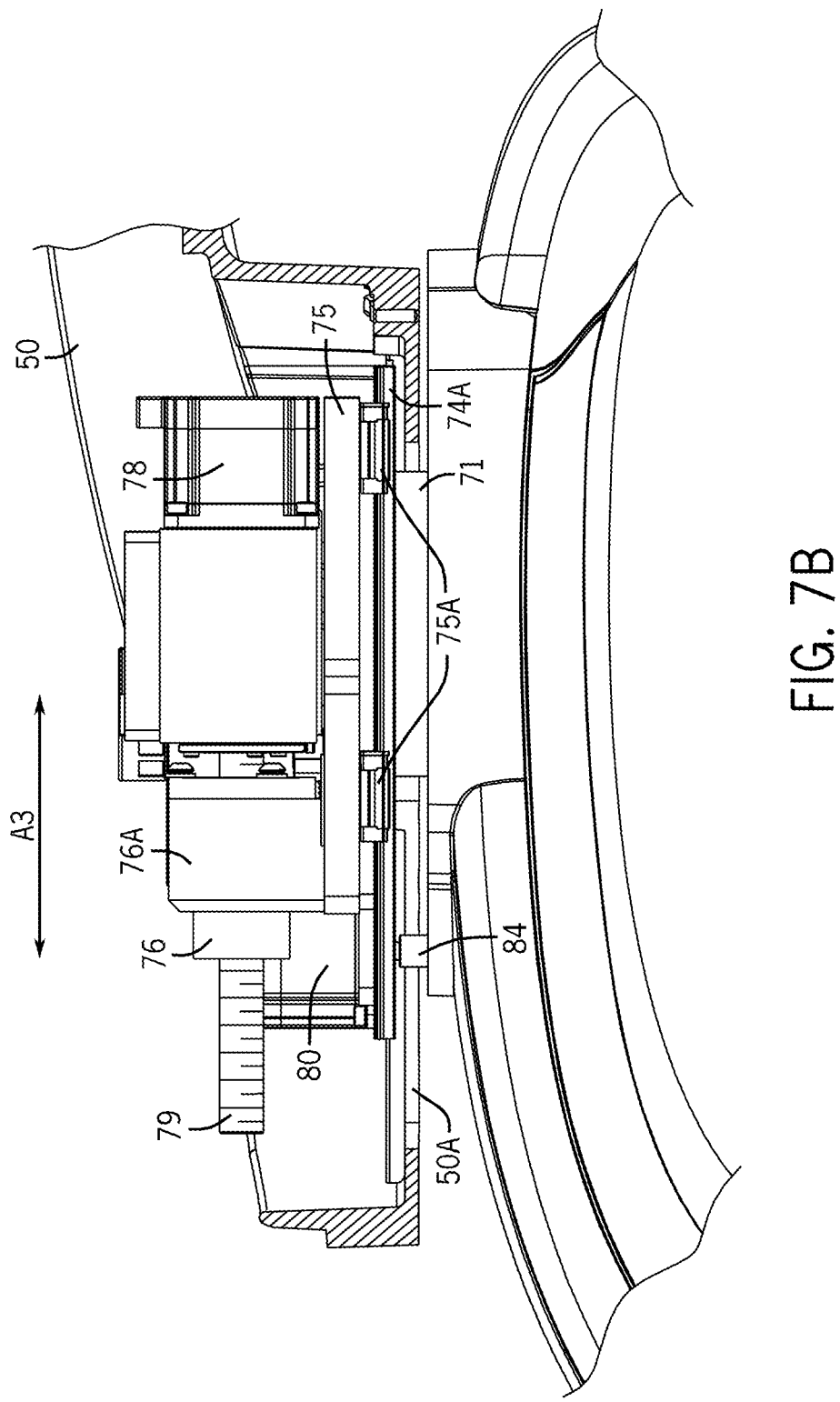
FIG. 7B is another cross sectional view of the panoramic dental radiation imaging system similar to FIG. 7, but in another alternate position to that shown in FIGS. 7 and 7A.
Figure 8:
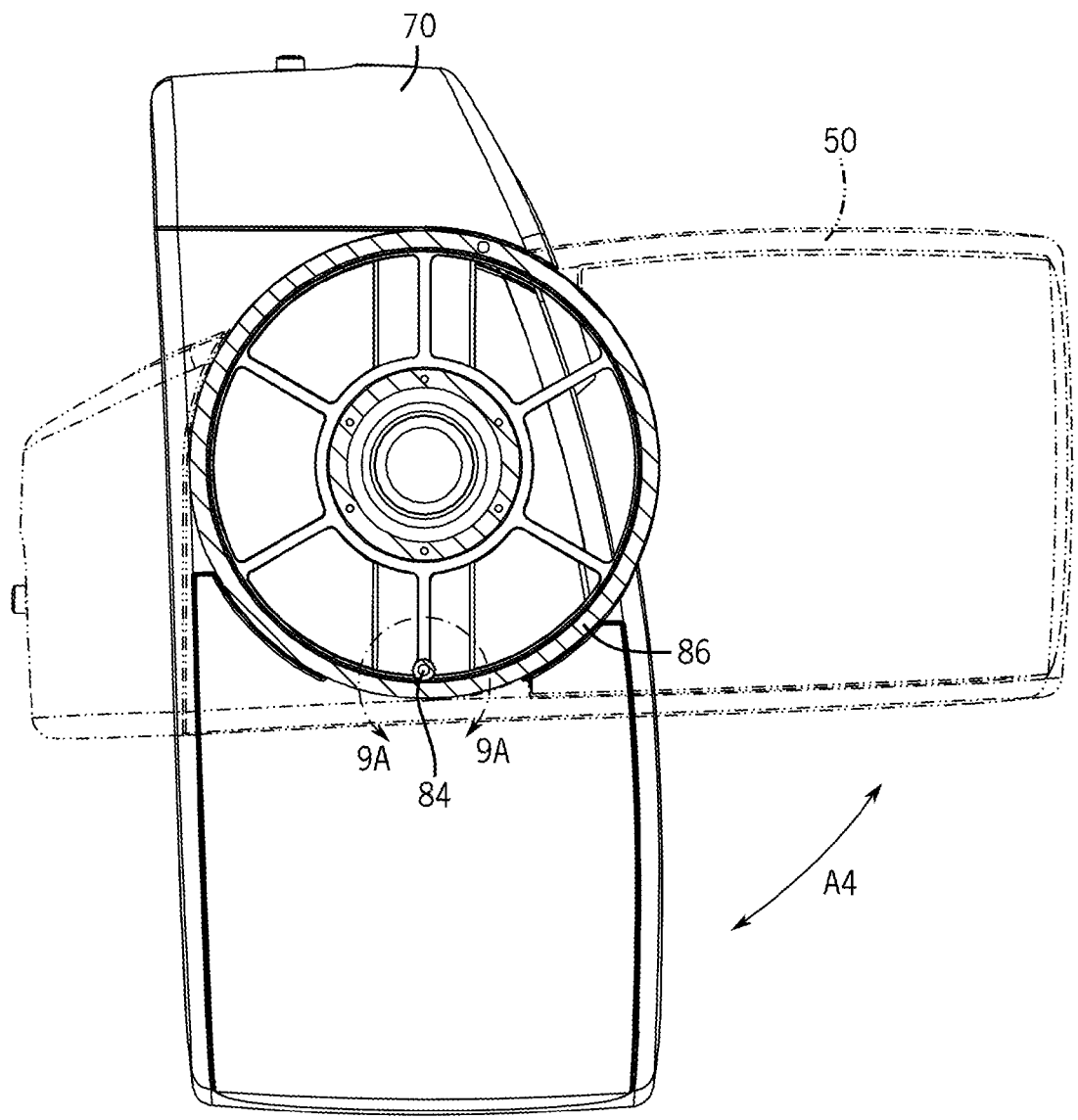
FIG. 8 is a bottom view of the C-arm of a panoramic dental radiation imaging system with the overhead arm shown in phantom.

Upright support 15, and specifically outer column 20, may be fixed to a floor 21 and/or a wall 22 by a support leg 23 to support the imaging system 10. Inner column 30 is preferably slidably coupled to outer column 20 to allow movement of the inner column 30 generally in the vertical direction, indicated by arrow A1 and as seen in FIG. 2. FIGS. 2 and 3 show the mechanism for vertical movement of the inner column 30. In the embodiment shown, threaded tube 32 is connected to inner column 30, and threaded rod 34 is connected to a base 24 to which outer column 20 is also connected. In this embodiment, tube 32 and rod 34 are threadedly engaged together. A motor 25, shown mounted on the base 24, rotates the rod 34, in this case by means of a gear reducer 26, so as to move the tube 32 up or down depending upon the direction of rotation. Since inner column 30 is connected to tube 32, the up or down movement of the tube moves the inner column up and down along with it, allowing patient positioning arm 40 and C-arm 70, including the radiation source 90 and radiation sensor 100, all coupled to inner column 30, to be raised or lowered to accommodate the height of the particular patient for which the radiation images are to be taken.

Thus, inner column 30 is adjusted to a height such that the patient's chin comfortably rests on the chin rest 42 and between the two positioning wands 43A, 43B. The patient positioning arm 40 ensures that the patient is properly aligned for positioning of the C-arm 70 including the radiation source 80 and receiver 90 for taking of a radiation image of the patient's teeth. A movable mirror 44 may be coupled to inner column 30 to further aid in proper patient positioning, in the sense that, from the side, an operator may see the alignment of the patient's face with respect to the patient positioning arm 40. A display screen 46 may also be movably coupled to patient positioning arm 40 for readout of positioning, radiation activity, imaging, and other desired information to the operator or technician of the imaging system 10.

The motion system of the imaging system 10 is further shown in FIGS. 4-8. The motion system provides movement of the radiation source 90 and radiation sensor 100 in several directions: movement of the overhead arm 50 in a rotational direction shown by the arrow A2 in FIGS. 1 and 4; movement of the C-arm 70 in a direction axial to the overhead arm 50 shown by the arrow A3 in FIGS. 1, 7, 7A and 7B; and movement of the C-arm 70 in a rotational direction shown by arrow A4 in FIGS. 1 and 8. This multi-directional motion allows for precise positioning of the radiation sensor 90 and receiver 100 to provide precise radiation results for each patient and the ability to take radiations at various positions.

In the embodiment shown in FIGS. 4, 5A, 5B, 5C and 5D, overhead arm 50 is rotatably coupled to inner column 30 by means of an overhead mount 52 being coupled to an overhead bearing shaft 54 using an overhead locking ring 55. This assembly allows overhead arm 50 to rotate with respect to inner column 30 by permitting overhead mount 52 to rotate about the bearing shaft 54 in the direction indicated by arrow A2. To bring about rotational movement of overhead arm 50 with respect to the inner column 30, a linear actuator 59 is provided. One end 59A of the linear actuator 59 is rotatably connected to the overhead mount 52, offset by a suitable distance from the overhead bearing shaft 54. The opposite end 59B of linear actuator 59 is rotatably connected to the overhead arm 50, at a further distance from the overhead bearing shaft 54.

In the most preferred embodiment, as shown in the drawing figures, linear actuator 59 includes a motor drive link 56, mounted on the overhead mount 52 by means of a link pivot shaft 57 and a link locking ring 58, and offset as indicated above by a suitable distance from the overhead bearing shaft 54. A motor 60, such a stepper motor or other suitable motor to provide precise and controlled movement, is coupled to motor drive link 56 by any suitable removable connectors such as brackets 61A, 61B. A screw 62 is coupled to and driven by motor 60, such that activation of the motor rotates the screw. The screw 62 is engaged with a nut 66 which is mounted in a nut housing 68, and the nut housing 68 is fixed to overhead arm 50. Thus when motor 60 is activated, screw 62 rotates and moves through fixed nut 66 in the direction shown by arrow A5, FIGS. 5B and 5C. This shortens or lengthens the distance D1 between motor 60 and nut housing 68, as can be seen by comparing FIGS. 5A, 5B, 5C and 5D. Because the nut 66 is stationary with respect to the overhead arm 50, to accommodate this change in distance, a rotation of the motor drive link 56 occurs about the link pivot shaft 57. And in turn a rotation of the overhead mount 52 about the overhead bearing shaft 54 also occurs, thereby resulting in rotation of the overhead arm 50 with respect to inner column 30, in the direction A2. Thus, the offset of the motor drive link 56 from the bearing shaft 54 connected to the inner column 30 allows for rotation of the entire overhead arm 50 using a simplified rotational operation (a motor 60 rotating a screw 62) over that in existing panoramic radiation systems.

In addition to the rotation of the overhead arm 50, the imaging system 10 preferably also includes motion of the C-arm 70. The motion systems for movement of the C-arm 70 can be seen in FIGS. 6-9. As shown there, an attachment housing 71 is coupled to C-arm 70 and to overhead arm 50, in such a way that C-arm 70 is enabled to move in the x-axis direction (shown by arrow A3 in FIG. 1). Additionally, a C-arm bearing 72 coupled to C-arm 70 fits within attachment housing 71 and allows rotation in the A4 direction.

Specifically in the embodiment shown, a pair of rails 74A, 74B are attached to overhead arm 50, in the area of the distal end of the overhead arm. The rails 74A, 74B straddle a slot 50A formed in a bottom face of the overhead arm. A carriage plate 75 is coupled to attachment housing 71, with one or more runners 75A provided to the carriage plate and engaged with a respective one of the rails 74A, 74B, such that carriage plate 75 is movable along the rails in the direction A3, and thus moves the entire C-arm 70 along that direction. A linear actuator 77 is provided to move carriage plate 75 in direction A3. In the embodiment shown, the linear actuator 77 includes a nut 76 mounted on carriage plate 75 by means of a nut housing 76A. In this embodiment the linear actuator 77 further includes a motor 78, which is affixed to overhead arm 50 by plate 78A. The shaft 78A of the motor 78 is coupled to a screw 79 which is engaged with nut 76, so that activation of the motor rotates the screw within the nut, and thus moves the nut closer to or further from the motor. Because nut 76 is coupled to the movable carriage plate 75 and the carriage plate is coupled to the C-arm 70 at the attachment housing 71, when the motor 78 rotates the screw 79, the motor remains stationary with respect to the overhead arm 50, while carriage plate, the attachment housing 71 and the entire C-arm 70 moves one way or the other along the direction A3. This apparatus for moving C-arm 70 is extremely simple, reliable, low noise, and repeatable, all very desirable characteristics in a dental imaging apparatus.

As described above, attachment housing 71 is coupled to C-arm 70 and to overhead arm 50, such that C-arm 70 is able to move in the x-axis direction (shown by arrow A3 in FIG. 1) as attachment shaft 71 moves in this direction within the slot 50A. To at the same time have the capability of moving C-arm 70 in the rotational direction indicated by arrow A4, a motor 80 is coupled to carriage plate 75 by means of a motor mount plate 82, so that it moves along arrow A3 with the vertical axis of the C-arm. Motor 80 is drivingly coupled to a rotatable wheel 84, which bears on or engages with the inner wall 86 of the upper surface of the C-arm 70. When the motor 80 is activated, causing the wheel 84 to rotate, the rotation of the wheel, bearing on inner wall 86, causes rotation of the C-arm 70 in direction A4 about the C-arm bearing 72.

Figure 9A:
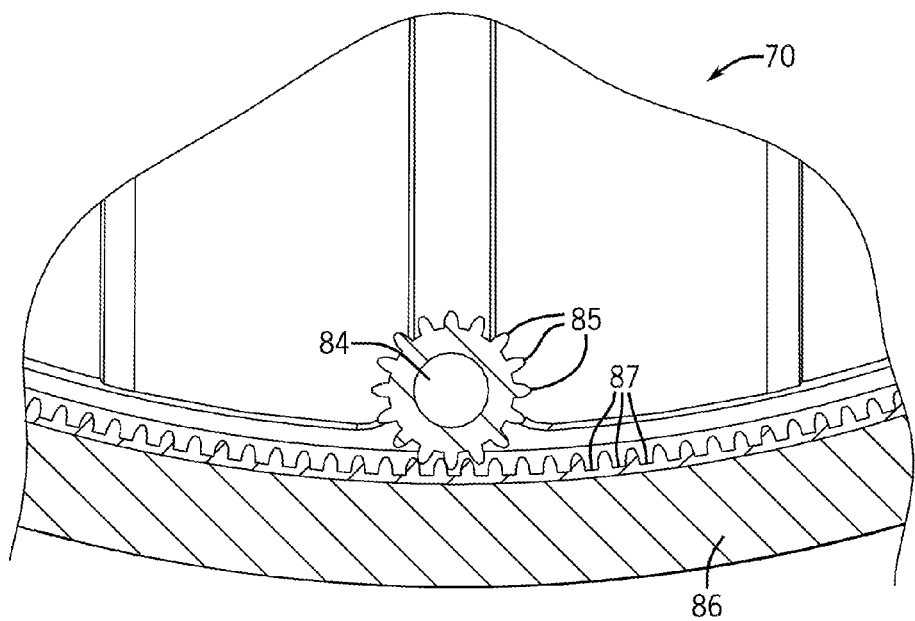
FIG. 9A is a detail view, partially in section, of a portion of a C-arm and rotatable shaft of a panoramic dental radiation imaging system in accordance with one embodiment of the present invention.

In one embodiment, shown in FIG. 9A, the wheel 84 is provided with teeth 85. Meshing teeth 87 are formed on or provided to inner wall 86. Teeth 87 are sized and shaped to engage with the teeth 85 of wheel 84. Again, when the motor 80 is activated, causing the wheel 84 to rotate, the teeth 85 of the wheel engage the teeth 87 of the inner wall 86 causing rotation of the C-arm 70 in direction A4 about the C-arm bearing 71. In one embodiment, teeth 85 engage with teeth 87 integrally formed on the inner wall 86. In any event, by this means, the C-arm 70 is thus capable of being moved in both an x-axis direction, and also in a rotational direction, while attached to the movable overhead arm 50.

Figure 9B:
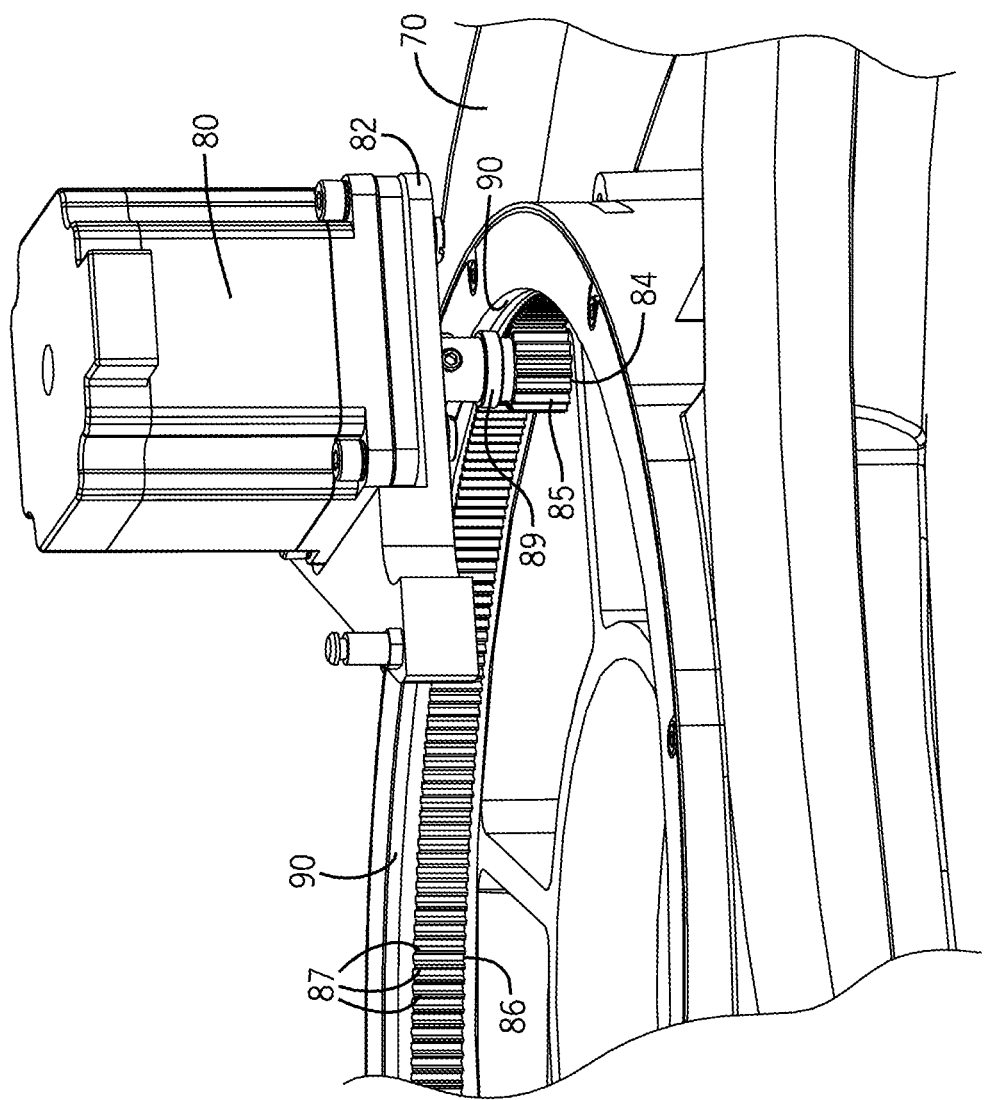
FIG. 9B is a perspective view, partially cut away, a portion of a C-arm and rotatable shaft of a panoramic dental radiation imaging system in accordance with one embodiment of the present invention.

In a variation of the embodiment of FIG. 9A, which variation is shown best in FIG. 9B, wheel 84 is provided with a special contact surface 89 axially spaced from teeth 85, and inner wall 86 is similarly provided with a separate contact surface 90 axially spaced from teeth 87 and aligned with contact surface 89. In operation, contact surface 89 and contact surface 90 contact each other. The engagement of these contact surfaces 89, 90 acts to control the center-to-center distance of wheel 84 and inner wall 86, so as to provide precise gear positioning and prevent overmeshing of the teeth 85 with the teeth 87. This arrangement drastically reduces system vibration generated by external forces holding the teeth 85 in mesh with teeth 87. This apparatus for rotating the C-arm gives precise control over gear mesh vibration and backlash, increases image quality and increases product life, because image quality does not degrade as quickly as with prior art systems, because of reduced wear and tear on the components. While there are small gaps shown in FIG. 9A between the back sides of the teeth 85 and the teeth 87, these gaps are in fact preferably very small, a few thousandths of an inch, just so as to avoid the overmeshing referred to above.

The most preferred form of radiation referred to in this description is x-ray radiation, but there may be other types of radiation, whether now known or later discovered, that would work as well.

Although the invention has been herein described in what is perceived at the time of writing to be the most practical and preferred embodiments, it is to be understood that the invention is not intended to be limited to the specific embodiments set forth above. Rather, it is recognized that modifications may be made without departing from the spirit or intent of the invention and, therefore, the invention is to be taken as including all reasonable equivalents to the subject matter of the appended claims and the description of the invention herein.

What is claimed is:

1. A panoramic dental radiation imaging system, comprising:
   a. a radiation source;
   b. a radiation sensor, capable of receiving and detecting radiations;
   c. a C-arm to which the radiation source and radiation sensor are mounted in a manner such that the radiation sensor is positioned so as to receive and detect radiations from the radiation source;
   d. an overhead arm to which the C-arm is rotatably mounted;
   e. a support column to which the overhead arm is rotatably mounted; and
   f. a linear actuator for moving the C-arm axially with respect to the overhead arm.

2. A panoramic dental radiation imaging system as recited in claim 1 further comprising rotating apparatus for rotating the overhead arm with respect to the support column.

3. A panoramic dental radiation imaging system as recited in claim 2 wherein the overhead arm is rotatably mounted to the support column at a rotation point, and wherein the apparatus for rotating the overhead arm comprises a linear actuator, having two ends, one end being connected to the support column at a point spaced apart from the rotation point, and the other end being connected to the overhead arm at a point spaced apart from the rotation point.

4. A panoramic dental radiation imaging system as recited in claim 1 further comprising a C-arm rotation motor mounted to the overhead arm, and driving a wheel, the wheel engaged with the C-arm such that the rotation of the wheel causes rotation of the C-arm.

5. A motion system for use in a panoramic dental radiation imaging system, the panoramic dental radiation system comprising a radiation source, a radiation sensor, capable of receiving and detecting radiations, a C-arm to which the radiation source and radiation sensor are mounted in a manner such that the radiation sensor is positioned so as to receive and detect radiations from the radiation source, an overhead arm to which the C-arm is rotatably mounted; and a support column to which the overhead arm is rotatably mounted, the motion system comprising:

a. apparatus for rotating the overhead arm with respect to the support column;

b. apparatus for rotating the C-arm with respect to the overhead arm, and c. apparatus for moving the C-arm axially with respect to the overhead arm.

6. A motion system as recited in claim 5 wherein the overhead arm is rotatably mounted to the support column at a rotation point, and wherein the apparatus for rotating the overhead arm comprises a linear actuator, having two ends, one end being connected to the support column at a first point spaced apart from the rotation point, and the other end being connected to the overhead arm at a second point spaced apart from the rotation point and from the first point.

7. A motion system as recited in claim 5 wherein the apparatus for rotating the C-arm with respect to the overhead arm includes a C-arm rotation motor mounted to the overhead arm, and driving a wheel, the wheel engaged with the C-arm such that the rotation of the wheel causes rotation of the C-arm.

8. A motion system as recited in claim 5 further comprising a linear actuator for moving the C-arm axially with respect to the overhead arm.

\* \* \* \* \*